(12) United States Patent
Shanks

(10) Patent No.: US 11,020,236 B2
(45) Date of Patent: Jun. 1, 2021

(54) SPINAL IMPLANT

(71) Applicant: T. S. Shanks, PLLC, Union City, TN (US)

(72) Inventor: Todd Shanks, Prospect, KY (US)

(*) Notice: Subject to any disclaimer, the term of this patent is extended or adjusted under 35 U.S.C. 154(b) by 165 days.

(21) Appl. No.: 16/524,022

(22) Filed: Jul. 27, 2019

(65) Prior Publication Data

US 2020/0000605 A1 Jan. 2, 2020

(51) Int. Cl.
*A61F 2/44* (2006.01)
*A61F 2/30* (2006.01)
*A61F 2/46* (2006.01)
*A61B 17/70* (2006.01)

(52) U.S. Cl.
CPC ............ *A61F 2/442* (2013.01); *A61F 2/3094* (2013.01); *A61F 2/4455* (2013.01); *A61F 2/4611* (2013.01); *A61B 17/7062* (2013.01); *A61F 2002/30733* (2013.01)

(58) Field of Classification Search
CPC .......... A61F 2/44; A61F 2/442; A61F 2/4455; A61F 2/46; A61F 2/4611; A61F 2/30; A61F 2/3094
See application file for complete search history.

(56) References Cited

U.S. PATENT DOCUMENTS

| | | |
|---|---|---|
| 6,159,211 A | 12/2000 | Boriani et al. |
| 6,743,255 B2 | 6/2004 | Ferree |
| 6,746,484 B1 | 6/2004 | Liu et al. |
| 2004/0133279 A1 | 7/2004 | Krueger et al. |
| 2005/0119753 A1* | 6/2005 | McGahan ............. A61F 2/4465 623/17.16 |
| 2014/0121776 A1* | 5/2014 | Hunt ..................... A61F 2/2803 623/17.16 |
| 2016/0310294 A1 | 10/2016 | McConnell et al. |

FOREIGN PATENT DOCUMENTS

WO WO2001085069 11/2001

* cited by examiner

*Primary Examiner* — Christopher J Beccia
(74) *Attorney, Agent, or Firm* — Business Patent Law, PLLC

(57) ABSTRACT

The present invention is an implant for bone. The current implant is particularly useful in spinal surgical procedures.

19 Claims, 3 Drawing Sheets

SPINAL IMPLANT

PRIORITY

Applicant claims the benefit of U.S. Provisional Patent Application No. 62/816,071—Spinal Implant—filed on Mar. 9, 2019.

BACKGROUND OF THE INVENTION

A. Field of the Invention

Among other things, the present invention is an implant for bone. The current implant is particularly suited for implantation into mammalian spinal tissues. The novel and nonobvious structures of the present spinal implant are particularly useful for lumbar or the lumbar/sacral surgeries.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) US Published Patent Application 20040133279—Krueger, et al. discloses surgical implants for use as spinal spacers; 2) US Published Patent Application 20050119753—McGahan, et al. discloses anterior impacted bone graft and driver instruments; 3) World Intellectual Property Organization Published Patent Application No. WO2001085069—Scient'X; 4) US Published Patent Application 20160310294—McConnell, et al. discloses a spinal fusion implant for oblique insertion; 5) U.S. Pat. No. 6,159,211—Boriani, et al. a stackable cage system for corpectomy/vertebrectomy; 6) U.S. Pat. No. 6,743,255—Ferree discloses a spinal fusion cage with lordosis correction; and 7) U.S. Pat. No. 6,746,484—Liu, et al. discloses a spinal implant.

Among other things, none of the above listed references disclose an implant adapted for implantation into a surgically created cavity in a spine; the implant comprising: an aperture bordered by twelve erect edges; the erect edges comprising six straight edges and a curved edge positioned between each straight edge such that the aperture extends through a superior planar supporting surface and an inferior planar supporting surface, wherein ends of the superior linear planar supporting surface and the inferior linear supporting surface, distant from a surgical incision allowing passage of the implant into a portion of the surgically created cavity, converge toward each other to create a lordotic angle.

SUMMARY OF THE INVENTION

The present invention provides a biocompatible implant for bone. Preferred embodiments of the implant are provided with an aperture. The aperture can assist tissue growth, such as bone, into and through the implant as well onto the inward surfaces of the implant. Select preferred embodiments of the current implant can also be utilized for transporting biocompatible devices/substances, such as adhesives, cameras, cannulas, fiber optics, implants, pharmaceuticals, etc. Some preferred embodiments of the implant can be provided with surface treatments in anticipation of improving attachment of bone to the implant.

It is believed that prior to the current invention, prior art implants for surgeries associated with the lumbar or the lumbar/sacral vertebral regions of the spine required rotation of the prior art implants subsequent to the surgical incision and before implantation into the surgically created cavity. It is also believed that elimination of rotation required by prior art lumbar or lumbar/sacral implants can reduce the possibility of surgical errors.

Insertion of the current implant into the surgically created cavity does not require specially manufactured insertion devices. The present spinal implant can be inserted into the surgically created cavity in a direct straight fashion with requiring turning maneuvers to position the implant in the surgically created cavity. Preferred embodiments of the current implant have a lordotic angle for engaging the surgically created cavity. The spinal implant can be specifically adapted for an oblique trajectory insertion into the surgically created cavity. It is believed that the unique and nonobvious slope of the implant provides variable degrees of lordosis in the trajectory where lordosis is required.

An aspect of the present invention is to provide an implant with a lordotic angle.

Still another aspect of the present invention is to provide an implant with twelve distinct regions surrounding an aperture.

It is still another aspect of the present invention to provide an implant that can be implanted, without rotation, through the surgical incision and into the surgically created cavity.

A preferred embodiment of the current invention can be described as an implant adapted for implantation into a surgically created cavity in a lumbar or lumbar/sacral vertebral region; the implant comprising: a) a superior linear planar supporting surface comprising a first end proximate a surgeon and a second end opposite from the first end; b) an inferior linear planar supporting surface comprising a first end proximate the surgeon and a second end opposite from the first end; c) an aperture bordered by twelve erect edges; the twelve erect edges comprising six straight edges and a curved edge positioned between each straight edge such that the aperture extends through the superior linear planar supporting surface and the inferior linear supporting surface; and d) the twelve erect edges extending between the inferior linear planar supporting surface and the superior linear planar supporting surface further comprising: i) a first region including two straight edges and a connecting curved edge; the first region having the greatest height; ii) a second region including two straight edges and a connecting curved edge; the second region having the least height, wherein the second region is opposed from the first region; iii) a third region including a straight edge and two connected edges opposed from a fourth region including a straight edge and two connected curved edges, wherein the interconnected first, second, third and fourth regions create a lordotic angle such that the implant is adapted for insertion through a surgical incision, without rotation, into the surgically created cavity, and wherein the second region is proximate a portion of the surgically created cavity most distant from the surgical incision.

Another preferred embodiment of the current invention can be described as a polyhedronal implant adapted for implantation into a surgically created cavity; the polyhedronal implant comprising: a) an aperture bordered by twelve edges; the twelve edges comprising six straight edges and a curved edge positioned between each straight edge such that the aperture extends through a superior linear planar supporting surface and an inferior linear supporting surface; and b) the twelve edges extending between the inferior linear planar supporting surface and the superior linear planar supporting surface further comprising: i) a first combination of two straight edges and a curved edge; the first combination having the greatest height; ii) a second combination of two straight edges and a curved edge opposed from the first combination; the second combination having the shortest height; wherein ends of the superior linear planar supporting surface and the inferior linear supporting surface converge toward each other as the supporting surfaces approach the second combination, and wherein the second combination is adapted for positioning proximate a portion of the surgically created cavity most distant from the surgical incision; and iii) a third combination of a straight edge and two curved edges opposed from a fourth combination of a straight edge and two curved edges; the third and fourth combinations disposed between the first and second combinations.

Still another preferred embodiment of the current invention can be described as an implant adapted for implantation into a surgically created cavity in a mammalian spine; the implant comprising: a) an aperture bordered by twelve edges; the twelve edges comprising six straight edges and a curved edge positioned between each straight edge such that the aperture extends through a superior planar supporting surface and an inferior planar supporting surface; and b) the twelve edges extending between the inferior planar supporting surface and the superior planar supporting surface further comprising: i) a first combination including two straight edges; ii) a second combination including two straight edges; the second combination opposite from the first combination, wherein ends of the superior linear planar supporting surface and an inferior linear supporting surface converge toward each other as the supporting surfaces approach the second combination; iii) a third combination including one straight edge and two curved edges; and iv) a fourth combination, opposite the third combination, including one straight edge and two curved edges.

Yet still another preferred embodiment of the current invention can be described as an implant adapted for implantation into a surgically created cavity in a spine; the implant comprising: an aperture bordered by twelve erect edges; the erect edges comprising six straight edges and a curved edge positioned between each straight edge such that the aperture extends through a superior planar supporting surface and an inferior planar supporting surface, wherein ends of the superior linear planar supporting surface and the inferior linear supporting surface, distant from a surgical incision, converge toward each other to create a lordotic angle.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant for bone where the implant can be adapted for connection with surgical tools. Examples of surgical tools adapted for connection with the implant include but are not limited to manual or robotic devices that assist with the implantation of the implant. Among other things, the current invention can be adapted for use with mammalian vertebra. It is believed that the present implant is particularly adapted for use in the lumbar or the lumbar/sacral vertebral region of the spine.

It is anticipated that the opening of the current invention can be used as a conduit for transporting biocompatible devices/substances, such as adhesives, cameras, cannulas, fiber optics, implants, pharmaceuticals, etc.

Preferred embodiments of the present invention are manufactured of titanium alloys, stainless steel, non-resorbable polymers or any other composition acceptable in the art. Manufacture of the current invention is compatible with 3D titanium printing.

Within the scope of the present invention, it has advantageously been discovered apertures of the implant range in size from about 400 millimeters$^2$ to about 1800 millimeters$^2$; widths of the implant range from about 20 millimeters to about 36 millimeters; lengths of the implant range from about 20 millimeters to about 50 millimeters; and heights of the apex of the implant range from about 8 millimeters to about 40 millimeters.

Figure 1:
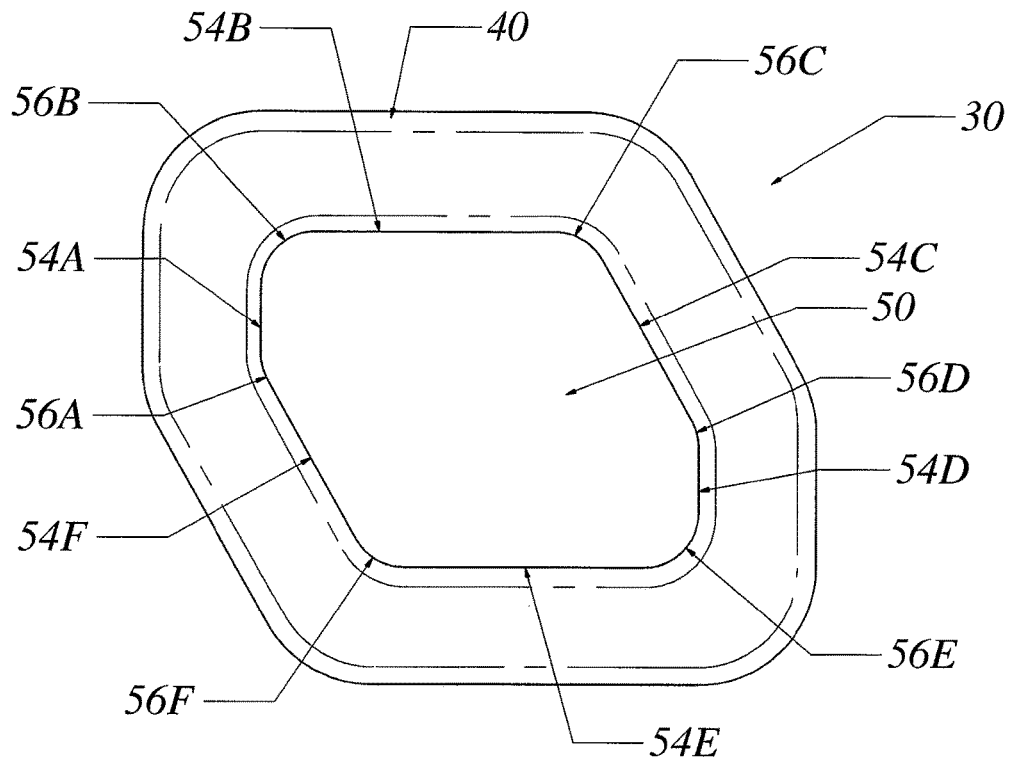
FIG. 1 is a top view of the implant.

FIG. 1 is a top view of a preferred embodiment of implant (30). As shown, superior load supporting surface (40) of implant (30) surrounds aperture (50). Preferred embodiments of superior load supporting surface (40) can be planar or linear planar.

Aperture (50) is formed by a plurality of straight erect edges (54 A-F) and curved erect edges (56 A-F). Preferred embodiments of the current implant (30) can have twelve interconnected erect edges (54 A-F, 56 A-F). Each straight edge (54 A-F) is interconnected with two opposed curved edges (56 A-F) and each curved edge (56 A-F) is interconnected with opposed straight edges (54 A-F).

Figure 2:
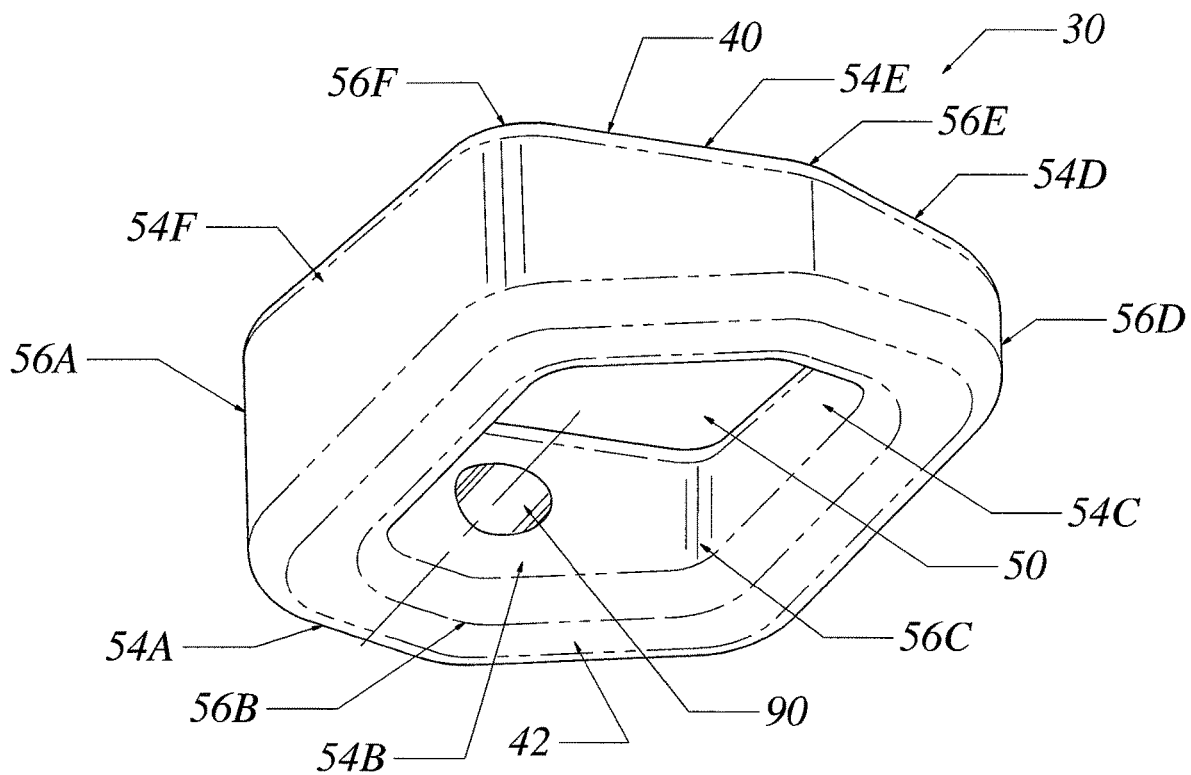
FIG. 2 is a first perspective of the implant.
Figure 3:
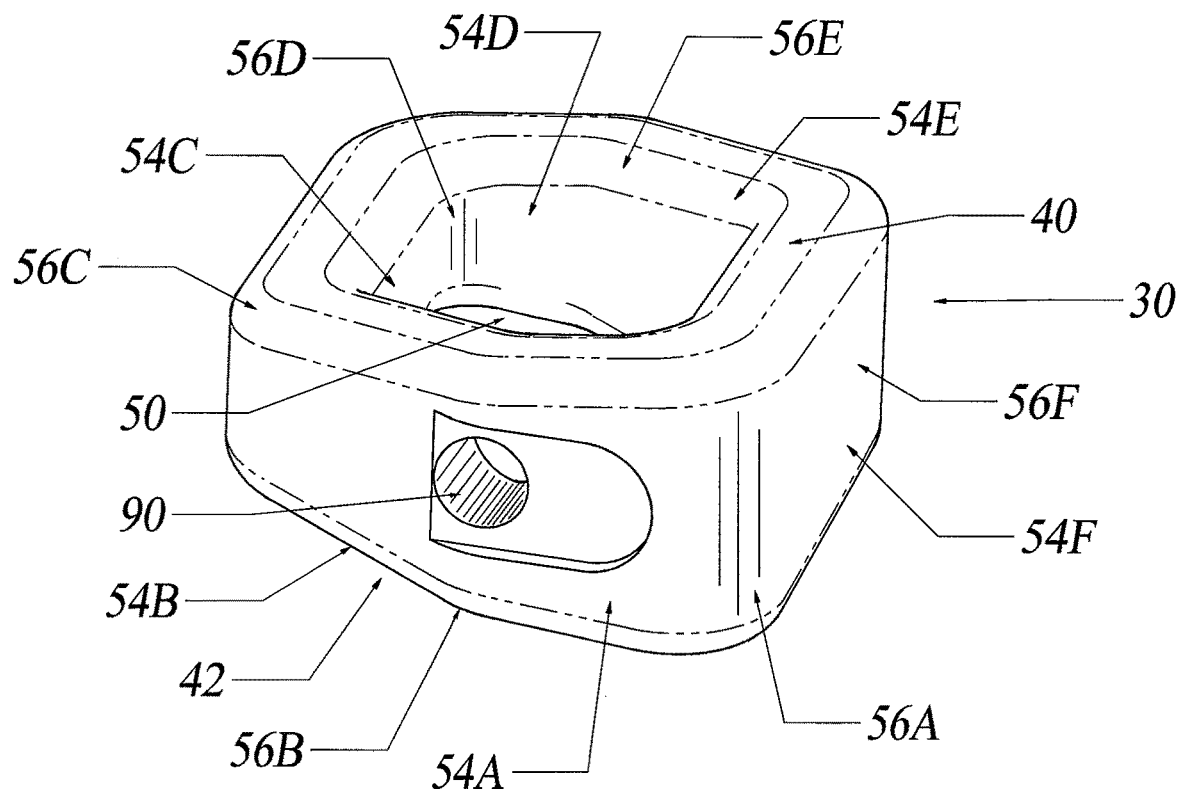
FIG. 3 is a second perspective of the implant.

FIGS. 2 and 3 are perspectives of implant (30). Aperture (50) extends through superior load supporting surface (40) and inferior load supporting surface (42) of implant (30). Preferred embodiments of inferior load supporting surface (42) can be planar or linear planar. Select preferred embodiments of implant's (30) load supporting surfaces (40, 42) are manufactured with uniform consistency causing exposed surfaces of implant (30) to have similar visual appearances and tactile sensations. At the same time, outer surfaces of implant (30) can be smooth, porous, rough, nano-coated or consist of a composite of biocompatible compositions such as hydroxyapatite or other bioactive substances. The twelve interconnected edges (54 A-F, 56 A-F) creating aperture can be isolated into regions or combinations that provide the innovative sloping structure of the present invention.

First region or combination (54F, 56A, 54A) of implant (30) has the greatest height of implant (30). Second region or combination (54C, 56D, 54D) opposite the first region or combination (54D, 56A, 54A) has the shortest height of implant (30). Third region or combination (56B, 54B, 56C,) is opposite from fourth region or combination (56E, 54E, 56F). Third region or combination and forth region or combination are positioned between the first and second regions. Superior load supporting surface (40) and inferior load supporting surface (42) converge toward each other as load supporting surfaces (40, 42) traverse from the first region or combination toward the second region or combination of implant (30). Select preferred embodiments of implant (30) include first, second, third and fourth combinations of erect edges (54 A-F, 56 A-F) that create a lordotic angle that allows implant (30) to be inserted, without rotation, through a surgical incision and into a surgically created cavity. For most surgical procedures using implant (30), it is anticipated that the second combination of solid edges will be distant from the surgical incision and the first combination of solid edges solid edges will be proximate the surgical incision. It is also anticipated that for most surgical procedures the second combination is adapted to be positioned proximate a portion of the surgically created cavity most distant from the surgical incision created for passage of the implant toward the surgically created cavity.

Within the scope of the current invention, erect edges (54 A-F, 56 A-F), aperture (50) and supporting surfaces (40, 42) create polyhedronal implant (30). Depending on engineering parameters, select preferred embodiments of implant (30) can be provided with opening (90) that extends through one of twelve erect edges (54 A-F, 56 A-F). Among other things, opening (90) is adapted for receiving a surgical tool (not shown in the drawings).

Figure 4:
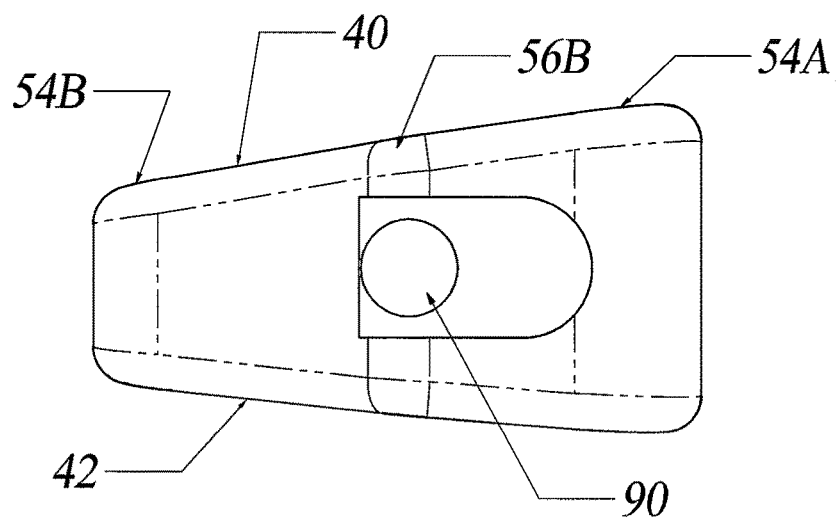
FIG. 4 is a frontal view of the opening for receiving a surgical tool including portions of the first and third combinations of solid edges of the current implant.

FIG. 4 is a frontal view of opening (90) adapted for receiving a surgical tool biocompatible devices/substances, such as adhesives, cameras, cannulas, fiber optics, implants, pharmaceuticals, etc. Portions of the first combination's erect edge (54B) and the third combination's erect edges (56B, 54B) of implant (30) disclose that load supporting surfaces (40, 42) are sloped from a higher to a lower height of implant (30).

Figure 5:
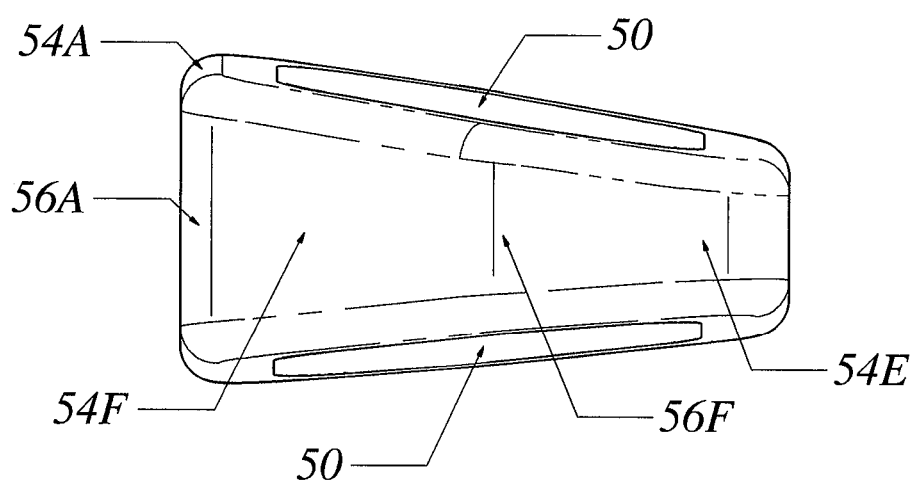
FIG. 5 is a lateral view of the implant.

FIG. 5 is a lateral view of implant (30) portraying a preferred embodiment of the current invention including a lordotic angle.

Applicant has enabled, described and disclosed the invention as required by Title 35 of the United States Code.

What is claimed is:

1. An implant adapted for implantation into a surgically created cavity in a lumbar or lumbar/sacral vertebral region; the implant comprising:
   a) a superior linear planar supporting surface comprising a first end proximate a surgeon and a second end opposite from the first end;
   b) an inferior linear planar supporting surface comprising a first end proximate the surgeon and a second end opposite from the first end;
   c) an aperture bordered by twelve erect edges; the twelve erect edges comprising six straight edges and a curved edge positioned between each straight edge such that the aperture extends through the superior linear planar supporting surface and the inferior linear supporting surface; and
   d) the twelve erect edges extending between the inferior linear planar supporting surface and the superior linear planar supporting surface further comprising:
      i) a first region including two straight edges and a connecting curved edge; the first region having the greatest height;
      ii) a second region including two straight edges and a connecting curved edge; the second region having the least height, wherein the second region is opposed from the first region;
      iii) a third region including a straight edge and two connected edges opposed from a fourth region including a straight edge and two connected curved edges, wherein the interconnected first, second, third and fourth regions create a lordotic angle such that the implant is adapted for insertion through a surgical incision, without rotation, into the surgically created cavity, and wherein the second region is proximate a portion of the surgically created cavity most distant from the surgical incision.

2. The spinal implant of claim 1 comprising an opening extending through one of twelve erect edges; the opening adapted to receive a surgical tool.

3. The spinal implant of claim 2, wherein the planar supporting surfaces have uniform consistency.

4. A polyhedronal implant adapted for implantation into a surgically created cavity; the polyhedronal implant comprising:
   a) an aperture bordered by twelve edges; the twelve edges comprising six straight edges and a curved edge positioned between each straight edge such that the aperture extends through a superior linear planar supporting surface and an inferior linear supporting surface; and
   b) the twelve edges extending between the inferior linear planar supporting surface and the superior linear planar supporting surface further comprising:
      i) a first combination of two straight edges and a curved edge; the first combination having the greatest height;
      ii) a second combination of two straight edges and a curved edge opposed from the first combination; the second combination having the shortest height; wherein ends of the superior linear planar supporting surface and the inferior linear supporting surface converge toward each other as the supporting surfaces approach the second combination, and wherein the second combination is adapted for positioning proximate a portion of the surgically created cavity most distant from the surgical incision; and
      iii) a third combination of a straight edge and two curved edges opposed from a fourth combination of a straight edge and two curved edges; the third and fourth combinations disposed between the first and second combinations.

5. The polyhedronal implant of claim 4 comprising an opening extending through one of the twelve edges; the opening adapted for receiving a surgical tool.

6. The polyhedronal implant of claim 5, wherein the converging load supporting surfaces create a lordotic angle.

7. The polyhedronal implant of claim 6, wherein the load supporting surfaces have uniform consistency.

8. The polyhedronal implant of claim 7 adapted for insertion into the surgically created cavity created in a lumbar or lumbar/sacral vertebral region.

9. The polyhedronal implant of claim 7 adapted for insertion through the surgical incision, without rotation, into the surgically created cavity.

10. An implant adapted for implantation into a surgically created cavity in a mammalian spine; the implant comprising:
    a) an aperture bordered by twelve edges; the twelve edges comprising six straight edges and a curved edge positioned between each straight edge such that the aperture extends through a superior planar supporting surface and an inferior planar supporting surface; and b) the twelve edges extending between the inferior planar supporting surface and the superior planar supporting surface further comprising:
   i) a first combination including two straight edges;
   ii) a second combination including two straight edges; the second combination opposite from the first combination, wherein ends of the superior linear planar supporting surface and an inferior linear supporting surface converge toward each other as the supporting surfaces approach the second combination;
   iii) a third combination including one straight edge and two curved edges; and
   iv) a fourth combination, opposite the third combination, including one straight edge and two curved edges.

11. The implant of claim 10 comprising, wherein the first combination has a greater height than the second, third and fourth combinations and the second combination has a lesser height than the first, third and fourth combinations, and wherein the third combination and the fourth combination are sloped from a greater height proximate the first combination to a lesser height proximate the second combination.

12. The implant of claim 11 comprising an opening extending through one of twelve edges; the opening adapted for receiving a surgical tool.

13. The implant of claim 12, wherein:
   a) the first, second, third and fourth combinations create a lordoic angle; and
   b) the planar supporting surfaces have uniform consistency.

14. The implant of claim 13 adapted for insertion into the surgically created cavity of a lumbar or lumbar/sacral vertebral region.

15. An implant adapted for implantation into a surgically created cavity in a spine; the implant comprising: a central aperture created by twelve erect edges; the created central aperture extending through a superior planar supporting surface and an inferior planar supporting surface and the erect edges comprising six straight edges and a curved edge positioned between each straight edge such that the created central aperture includes at least three distinct arcuate sections, wherein the superior linear planar supporting surface and the inferior linear supporting surface converge toward each other to create a lordotic angle.

16. The implant of claim 15, wherein the twelve erect edges comprise:
   a) a first combination including two straight erect edges;
   b) a second combination, opposite the first combination, including two straight erect edges;
   c) a third combination including one straight erect edge; and
   d) a fourth combination, opposite the third combination, including one straight erect edge, wherein the first combination has a greater height than the second, third and fourth combinations and the second combination has a lesser height than the first, third and fourth combinations.

17. The implant of claim 16 comprising an opening extending through one of twelve erect edges; the opening adapted for receiving a surgical tool.

18. The implant of claim 17 adapted for insertion into the surgically created cavity of a lumbar or lumbar/sacral vertebral region.

19. The implant of claim 18 adapted for insertion through the surgical incision, without rotation, into the surgically created cavity.

* * * * *